(12) United States Patent
Haupt et al.

(10) Patent No.: US 7,314,597 B2
(45) Date of Patent: Jan. 1, 2008

(54) CHEMICAL AGENT DETECTION

(75) Inventors: Steven Gerald Haupt, San Diego, CA (US); James Ha, San Diego, CA (US); David Rose, San Diego, CA (US)

(73) Assignee: Science Applications International Corporation, San Diego, CA (US)

( * ) Notice: Subject to any disclaimer, the term of this patent is extended or adjusted under 35 U.S.C. 154(b) by 254 days.

(21) Appl. No.: 10/842,436

(22) Filed: May 11, 2004

(65) Prior Publication Data

US 2005/0254996 A1    Nov. 17, 2005

(51) Int. Cl.
*C12Q 1/68*    (2006.01)
*B32B 5/02*    (2006.01)
*B32B 27/04*   (2006.01)
*B32B 27/12*   (2006.01)
*G01N 21/00*   (2006.01)

(52) U.S. Cl. ............ 422/83; 422/50; 422/58; 422/68.1; 422/100; 422/101; 436/43

(58) Field of Classification Search ........ 422/50, 422/58, 68.1, 100, 83, 101; 436/43
See application file for complete search history.

(56) References Cited

U.S. PATENT DOCUMENTS

| | | | |
|---|---|---|---|
| 4,759,210 A | 7/1988 | Wohltjen | 73/31.07 |
| 5,120,421 A | 6/1992 | Glass et al. | 204/406 |
| 5,571,401 A | 11/1996 | Lewis et al. | 205/787 |
| 6,017,440 A | 1/2000 | Lewis et al. | 205/777.5 |
| 6,308,130 B1 * | 10/2001 | Vojtisek-Lom | 701/114 |
| 6,345,234 B1 * | 2/2002 | Dilger et al. | 702/24 |
| 6,493,638 B1 | 12/2002 | McLean et al. | 702/22 |
| 6,931,913 B2 * | 8/2005 | Manoosingh | 73/31.01 |

OTHER PUBLICATIONS

"Handbook of Machine Olfaction—Electronic Nose Technology," Edited by T. C. Pearce, S. S. Schiffman, H. T. Nagle, and J. W. Gardner, Wiley-VCH Verlag GmbH & Co. KGaA Weinheim, Copyright 2003, (Cover, Copyright Page, Table of Contents—15 pp.), Chapter 11—"Electronic Tongues and Combinations of Artificial Senses," F. Winquist, C. Krantz-Rülcker, and I. Lundström, pp. 267-291.

International Search Report and Written Opinion for Application No. PCT/US05/06798, dated Sep. 15, 2006 (mailing date).

* cited by examiner

*Primary Examiner*—Brian Sines
(74) *Attorney, Agent, or Firm*—King & Spalding LLP

(57) ABSTRACT

A chemical agent detector with a lesser demand sensor, a greater demand sensor, an inlet; and a manifold; and methods associated therewith. The manifold is positioned between the inlet and the sensors, and includes a first intake associated with the lesser demand sensor, a second intake associated with a greater demand sensor, and at least one restrictor. The first intake is placed closer to the inlet than the second intake, and the second intake is isolated from the inlet by at least one restrictor within the manifold. The intakes and restrictor are sized and positioned such that the ratio between: the conductance of the path from the inlet to the greater demand sensor to the conductance of the path between the sensors effectively isolates the lesser demand sensor from the effects of the greater demand sensor.

15 Claims, 6 Drawing Sheets

Main Menu

Agent: Nerve-Sarin GB

Concentration: Low 0.4 mg/m³

Dose: 2.0 mg-min/m³

ICt50: 25mg-min/m3

---

Thu Dec 5 10:27: 8 2002 Fused Class: Nerve Type: Sarin GB Level: Medium Conc: 0.4 mg/m3 2.0 mg-min/m3 CTemp: 44.40 ExtTemp: 32.52 Hum: 3.87

---

SAW Data Stream

IM Celll Data Stream

Agent Class Identification Routine
Used to identify agent class type
410

→ Agent class to display/log
Nerve
Blister
Blood

Specific Agent Evaluation
The specific agent in within the agent class is identified
420

→ Agent type to display/log
Nerve (VX, GA, GB, GD, GF)
Blister (HD, HN-3)
Blood (AC)

Agent Quantification
Agent concentration in mg/m3 is displayed
430

→ Agent quantification to display/log
High, medium
mg/m³

Dose record 440
The cumulative exposure is sent to display and to the mission record. In addition, the ICt50- the incapacitation expose is also displayed as a reference → Agent dose to display/log
mg/m3
ICt50 value inmg/m³

Figure 4

| Sensor 2 | | | | | | | | | | | | Sensor 1 | | | | | | | | | | |
|---|---|---|---|---|---|---|---|---|---|---|---|---|---|---|---|---|---|---|---|---|---|---|
| Blood | | | Blister | | | Nerve | | | Clear | Fault | | Blister | | | Nerve | | | Blood | | | Clear | Fault |
| Low | Med | High | Low | Med | High | Low | Med | High | | | | Low | Med | High | Low | Med | High | Low | Med | High | | |
| | | | | | | | | | | | Fault | | | | | | | | | | | |
| | | | | | | | | | Blister | Blister | Clear | | | | | | | Blood | Blood | | | |
| | | | Blister | Blister | Blister | Nerve | | | | | High | | | | | | | | Blood | Blood | Nerve | |
| | | | Blister | Blister | Blister | Nerve | Nerve | Nerve | | | Med | | | | | | | Blood | Blood | Blood | | |
| | | | Blister | Blister | Blister | Nerve | Nerve | Nerve | | | Low | | | | | | | Blood | Blood | Blood | | |
| | | | | | | | Nerve | Nerve | | | High | | | | | | | | | | | |
| | | | | | | | | Nerve | | | Med | | | | | | | | | | | |
| | | | | | | | | | | | Low | | | | | | | | | | | |

CHEMICAL AGENT DETECTION

STATEMENT REGARDING FEDERALLY SPONSORED RESEARCH OR DEVELOPMENT

The U.S. Government may have certain rights in the disclosed invention as provided for by the terms of contract N41756-00-C-0911 awarded by the U.S. Government Combating Terrorism Technology Support Office, Technical Support Working Group.

BACKGROUND OF THE INVENTION

1. Field of the Invention

The present invention relates generally to methods and systems for the detection of chemical agents. More particularly, the present invention relates to the use of multiple types of chemical agent detectors having overlapping performance.

2. Description of Related Art

Sensors capable of detecting the presence of chemical agents and quantifying the amount of agent present are known. These sensors can be grouped into at least two types, e.g., analytical and phenomenological. Typically, an analytical sensor, such as a mass spectrometer, directly measures some characteristic of the environment, e.g., the mass and relative concentration of atoms or molecules. While capable of high accuracy and low false alarm rate, analytical sensors are typically expensive, cumbersome, and slow—requiring significant preparation and calibration activity.

Phenomenological sensors can be characterized as detecting an event which points to the presence of a chemical agent; e.g., a change in the resistance of a semiconductor that has been coated with a substance responsive to one or more specific chemical agents. Typical phenomenological sensors consist of an array of elements that can be trained to recognize patterns of phenomena. Existing sensors that can be characterized as phenomenological include Ion Mobility (IM) cells, chemo-resistive sensors, metal-oxide sensors, and Surface Acoustic Wave (SAW) devices. Some sensors of these types are capable of detecting several types of chemical agents, are relatively small (especially in comparison to analytical sensors), and potentially inexpensive in large quantities. However, these sensors have not displayed a false alarm rate required by many applications.

While sensor systems exist that combine more than one detection technology, the sensors in such existing systems have distinct, non-overlapping, capabilities. For example, the Hazmat CAD (Chemical Agent Detector) from Microsensor Systems, Inc. of Bowling Green Kentucky uses both a SAW and an electrochemical sensor. The two sensors have distinct capabilities. The electrochemical sensor only provides detection of hydrogen cyanide (HCN); it does not provide detection capability overlapping with the SAW.

Typical multi-sensor systems have not satisfactorily addressed issues related to airflow in devices comprising more than one sensor type—especially where different sensor types have different cycle times and flow requirements. Further, typical sensor systems are susceptible to contamination, aspiration of water, adsorption of volatiles that may later be out-gassed, and the uptake of potentially abrasive solid particles such as dirt, dust, or sand.

SUMMARY OF THE DISCLOSURE

In preferred embodiments, the invention includes a chemical agent detector with a a lesser demand sensor, a greater demand sensor, an inlet; and a manifold. The manifold is positioned between the inlet and the sensors, and includes a first intake associated with the lesser demand sensor, a second intake associated with a greater demand sensor, and at least one restrictor. The first intake is placed closer to the inlet than the second intake, and the second intake is isolated from the inlet by at least one restrictor within the manifold. In some embodiments, the intakes and restrictor are sized and positioned such that the ratio between: the conductance of the path from the inlet to the greater demand sensor to the conductance of the path between the sensors is greater than one—thereby effectively isolating the lesser demand sensor from the effects of the greater demand sensor. Depending on the specific sensors' duty cycle and volumetric requirements, the ratio can be substantially greater than one. For a preferred embodiment, a nominal value of 50 is effective.

In other embodiments, the invention includes a chemical agent detector comprising at least two sensors, a processor system, and a computer program product resident in memory. At least two of the sensors have overlapping effectiveness and provide both processed sensor data and raw sensor data. The sensors are in communication with the processor system. The computer program product is executable on the processor system and includes an agent class identification routine operable to determine the class of agent present based at least in part on the processed sensor data. In some embodiments, the processed sensor data comprises the alarm state of a plurality of sensors, and the detector determines the class of agent present at least in part by comparing the combined alarm state to a table of agent classification results. In further embodiments, the table of agent classification results is derived at least in part through elimination of false alarm modes as an influence on agent classification.

Some embodiments include a method for mitigating desensitization of the first sensor where the first sensor is operative to adjust its baseline to compensate for changes in ambient levels of a chemical agent and at least one second sensor not operative to so compensate. Where the first sensor has at least once adjusted its baseline, and where the second sensor indicates the presence of a chemical agent from among chemical agents common to the capabilities of both sensors and the first sensor does not indicate the presence of the chemical agent, the method includes adjusting the first sensor to a prior baseline and retaining the adjusted baseline if the first sensor alarms with the adjusted baseline.

BRIEF DESCRIPTION OF THE DRAWINGS

FIG. 4 illustrates process and information flow of a chemical agent detector of the present invention FIG. 5 is a table illustrating a first level of data fusion of the present invention.

DETAILED DESCRIPTION

As required, detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention.

Preferred embodiments of the invention include a chemical agent detection system using multiple sensors having overlapping performance, a tiered data fusion approach, a manifold configured to mitigate airflow problems presented by using multiple sensors having differing airflow requirements, and an inlet/outlet arrangement configured to mitigate the chance of contamination, aspiration, absorption/outgassing, abrasion, and the memory effect associated with operating multiple sensors having potentially different airflow requirements. Sensors mounted in a chassis draw an air sample through an inlet and a manifold, and then exhaust the air through an outlet. PFA Teflon™ fittings are provided to allow the system top to be attached to a variety of vapor generators.

Figure 1:
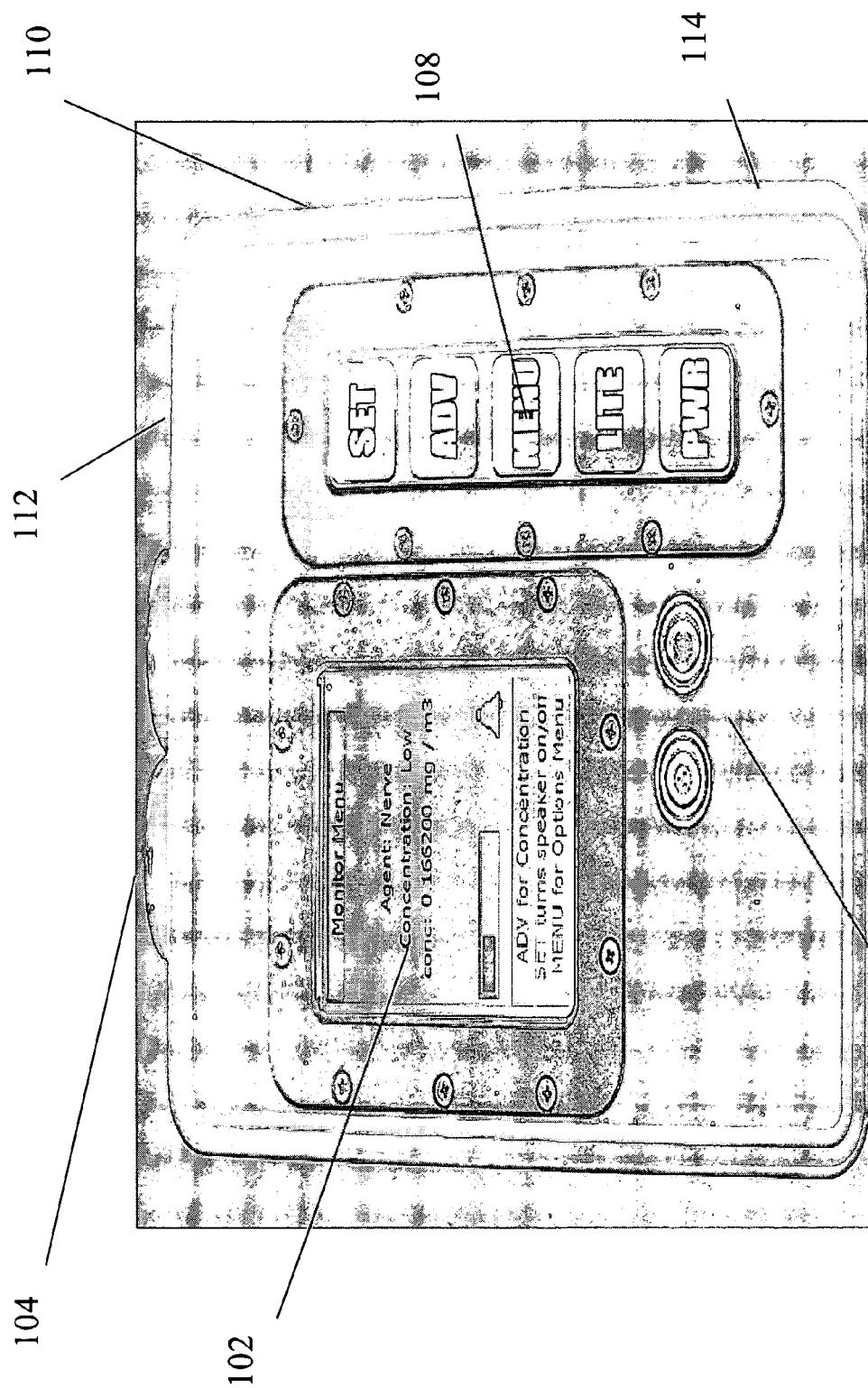
FIG. 1 illustrates a front panel view of a chemical agent detector of the present invention.

Referring to FIG. 1, a front view of an embodiment of the present invention is shown. In that embodiment, agent type and relative concentration are displayed on screen 102. Inlet (left) and outlet (right) 104 are on the top. Two front-panel connectors (available e.g., from LEMO USA Inc., Rohnert Park, Calif.) are for AC power (left) and RS-422 lines (right) 106. Commands can be entered via front keypad 108. Not shown on this figure are an Infrared Data Association (IrDA) port on the side 110 of the device, alarm and status (red and green respectively) light-emitting diodes (LEDs) on top face next to the outlet 112, and battery lid 114.

The chassis 116 is sized to be hand-held and in some embodiments is protected from electromagnetic interference by use of a conductive coating such as Electrodag 550® (available from, e.g., Acheson Colloids Company, Port Huron Mich.) or an aluminum case. For multipart chassis, o-rings are used to seal. A battery compartment is contained within the chassis and in preferred embodiments is sized to accept batteries such as AL 123, CR 123. Such batteries, or their equivalents, are selected to last over nine hours operating at room temperature. In preferred embodiments, the display is one such as the backlit, polycarbonate-protected Hitachi 1/4 VGA display. A processor card similar to those used in personal digital assistants (PDAs) is used in preferred embodiments. For example, some embodiments use the SA1110 chip set from InHand Electronics, Rockville Md. This is a Microsoft Windows CE-based computer system. A speaker is provided in preferred embodiments for, inter alia, audio alarms.

Embodiments of the present invention use a plurality of sensor types that at least in part provide overlapping areas of effectiveness. In addition to overlapping areas of effectiveness among sensor types, embodiments of the current invention use a tiered approach to data fusion that taps the synergy available in using more than one sensor technology. In preferred embodiments, the use of off-the-shelf sensors provides one tier—each sensor comes with detection routines of its own. These sensors provide both alarms (used to support one tier) and separately, raw data used as input to a second tier of data fusion. By using the vendor-supplied routines as a first tier, embodiments of the invention can leverage competitive advances in the underlying sensor technology. Preferred embodiments of the present invention, including the exemplary embodiment described herein, employ a SAW detector, e.g., HazmatCAD from Microsensor Systems, Inc., Bowling Green Kentucky, and an IM cell sensor, e.g., ChemPRO from Environics Oy, Mikkeli, Finland. Both sensors provide a processed response, e.g., alarms, and raw data. Other combinations of sensor technologies, e.g., chemoresistive and IMS for toxic industrial chemicals, can be combined in the fashion of this invention for both chemical agent detection, and detection of other substances, e.g., us of combined SAW/IMS to detect explosives. Such combinations are contemplated within the scope of the claims.

The SAW assembly includes four (4) surface acoustic wave sensors, each on a separate quartz chip. One chip is a reference; the other three are coated with polymers responsive to particular agents. Chemical sensing is achieved by noting frequency shifts as the polymer film absorbs the analyte. In addition, the SAW assembly includes an E-Chem Cell that separately is used to detect HCN. The IM Cell is typically more effective than SAW sensors on low molecular weight substances. The IM Cell includes a 16-channel IM Sensor Array and separate SemiConducting Cell (SCC) to detect blister agents.

Interferents such as household cleaning agents, fuels, an other items commonly found in the home, office, and garage are typical sources of false alarms in chemical agent detection systems. Other interferents include volatile organic compounds, organic acids, and toxic industrial materials found in many commercial settings. A SAW-SCCell/IMCell Multi-sensor embodiment of the present invention was exposed to headspace concentrations of agents such as these in a series of tests. In these tests, a vial containing approximately one to three milliliters of interferent was placed directly under the inlet of the system and the sensors were allowed to sample the headspace of the container for 40 seconds.

Of the 151 interferents examined, either the individual SAW or SCCell/IMCell displayed a strong response to 26 of the interferents and provide five false alarms. The false alarm rate after fusing data from the sensors in accordance with the present invention was one false alarm. Thus, the use of multiple sensors and data fusion in accordance with the present invention was shown to reduce false alarm rate by 75%. Results in field trials indicate that false alarms were reduced from a daily event to a once-a-year event.

Figure 2:
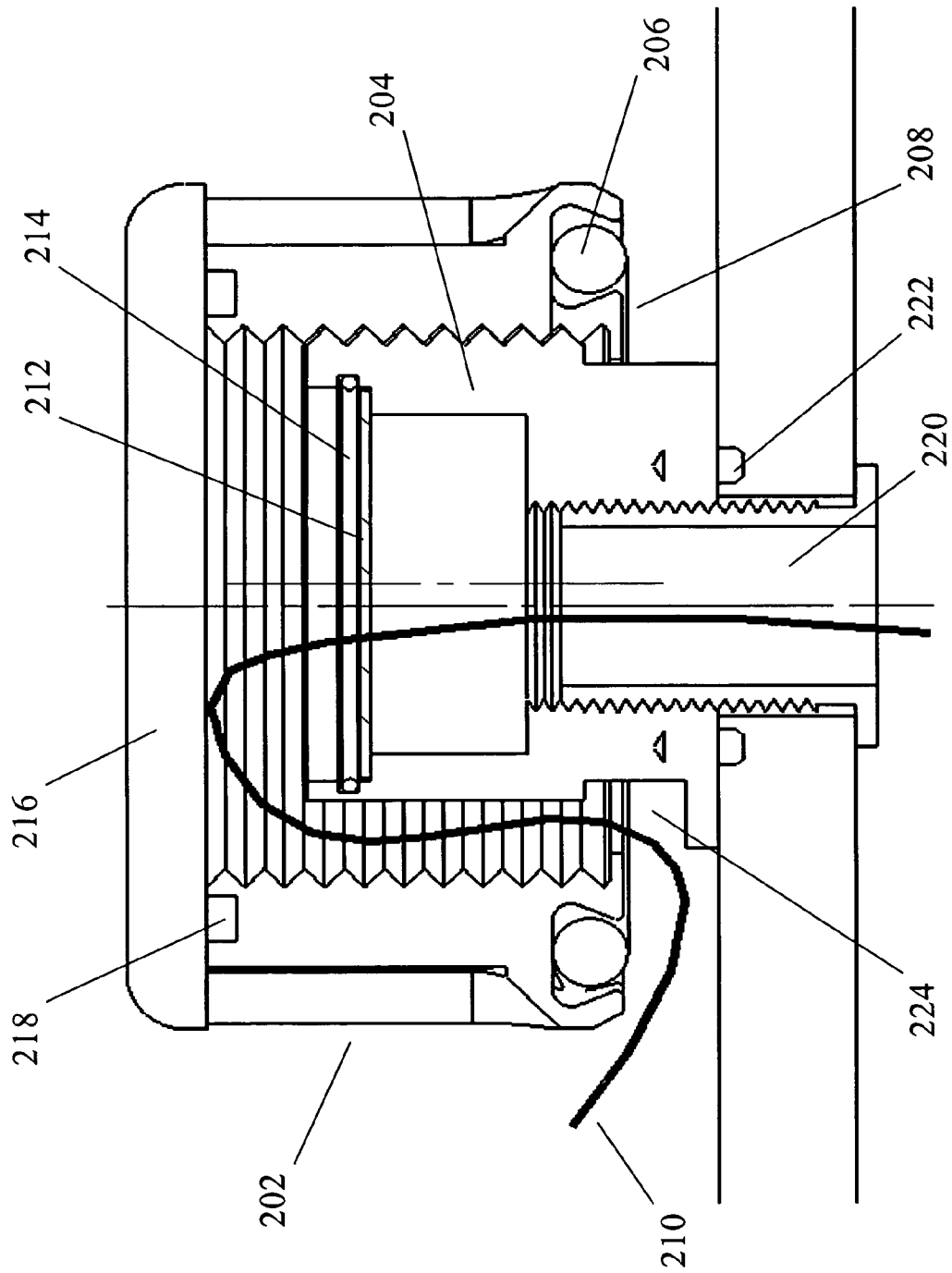
FIG. 2 illustrates an inlet/outlet port of a chemical agent detector of the present invention.

Referring to FIG. 2, an inlet/outlet port of preferred embodiments of the present invention is illustrated. For clarity, structural and operation features are described with respect to input. For output, the airflow traverses the opposite path. A cap 202 can be screwed up or down on a spud-like hollow cylinder 204 to open or close a gap for air intake. The cap 202 and spud 204 have a multiple start, high helix thread for traversing the gap in a half turn of the cap 202. A captured o-ring 206 seals to the sensor chassis 116 to provide a substantially water and air tight seal. A lip 208 provides a stop under the spud threads to prevent the cap from screwing off completely. Airflow traverses a path 210 from outside the inlet port through a partial cut away of the spud threads 212. It then passes through a filter 212 that is held in place by a spring clip 214. The filter can be changed by removing a cover 216 that is sealed to the cap by an o-ring 218. Air passes through a hollow fastener 220, which secures the inlet port to the sensor chassis 116, and then flows to the other portions of the sensor system, e.g., to the manifold. The spud 204 is prevented from rotating on the fastener 220 by pins 222 through the sensor chassis 116 and spud 204. This arrangement filters the air and mitigates against rain aspiration in any direction by shielding the intake gap with the cap, double backing the flow path, and providing a run-off channel 224 that conducts water around the spud before it can enter the cap.

Air passage surfaces are constructed of Teflon, Teflon-coated, or nickel-plated to mitigate adherence of volatiles. This combination of materials allows the use of Teflon (the preferred non-absorbing material but uncontrollable to accurate thickness) in most areas but provides for closely fitting moving mechanical parts such as the screw thread in the airway by the use of nickel plating (an acceptable non-absorbing material controllable to tight tolerances).

In preferred embodiments, a manifold supplies multiple sensors with air from one inlet source. The manifold balances the flow and volumetric demands of multiple sensors so that the higher demand is prevented from effectively diminishing the lower demand. In one fashion, this is accomplished by the design of obstructions/restrictions, cavities, and the placement of some sensor's connections away from the source. In preferred embodiments, a design process of placing the intake for the lower demand sensor in a cavity generally under the inlet and the higher demand sensor behind a restriction, calculating conductance based on the size/location of location and size of each element, and then varying the size to achieve a favorable ratio of path conductances is used.

Specifically, for a dual sensor system, the flow delivery is balanced by placing the intake of the lesser-demand sensor closer to the main inlet in proportion to the airway area, and conversely isolating the higher demand sensor by restrictors from the main inlet. The conductance of the manifold inlet and the gas path to the individual sensors is designed such that the calculated conductance of inlet to the high flow sensors is significantly larger than the conductance path between the individual sensors. In embodiment employing the Hazmat SAW and ChemPro IMCell sensors, a factor of 50 is preferred. Note that in preferred embodiments, the basic geometric relationships remain. Conductances are calculated based on the size and placement of at least the restriction to control the ratio of (conductance of the inlet to high flow sensor/conductance of the path between sensors) is greater than one, with the specific ratio of 50 being preferred for a SAW/IM Cell combination. The ratio can be determined empirically or by modeling.

Figure 3:
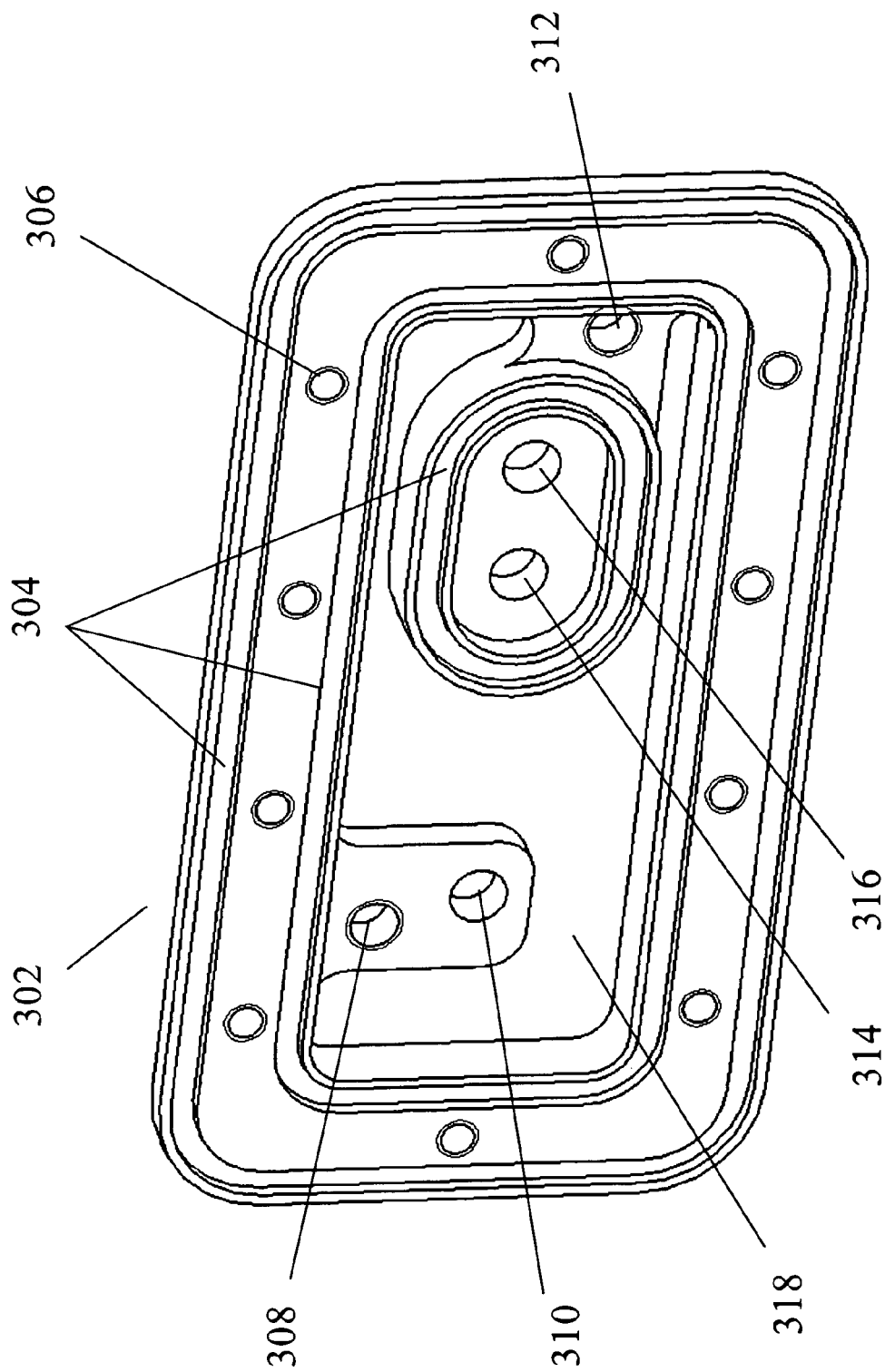
FIG. 3 illustrates a manifold of the present invention.

Referring to FIG. 3, a proportioning manifold of preferred embodiments of the current invention is illustrated. A manifold block 302 is sealable to the inside of a sensor enclosure (not shown) with o-rings (304*a*, *b*, and *c*-grooves shown only) and fastened with screws in tapped holes 306. Preferably, the manifold is constructed so that the tubing distance to the sensors is minimized and the tubing path is straight. This is to minimize the tubing surface area that might absorb and outgas, and because such a tubing material is inflexible. Tapped holes for pneumatic barbed fittings 308, 312 are in line with the sensors' intake ports. To monitor the air temperature, a hole 310 is provided for a thermistor. The exhaust from the sensors are connected to two holes 314, 316 with barbed fitting that are not necessarily in line with the sensors' exhaust ports as special tubing is not required. The exhaust portion of the manifold is sealed from the inlet portion with an o-ring. The position of the exhaust area is directly over the outlet port of the unit (described above). Similarly, the inlet port of the unit (described above) is directly over the sensor with the low airflow demand 312. The sensor with the high airflow demand 308 has restricted airflow to the main inlet. In this case, the exhaust area provides the restriction. A large volume 318 is proved for the sensors to draw from, so that the affect of the high demand sensor further diminished.

In preferred embodiments, a data fusion method evaluates alarms generated by the sensors to determine the class of agent(s) present (first tier); then (second tier) uses raw data from the sensors to identify the specific agent within the class, quantify the identified agent, and track dosage over time. Referring to FIG. 4, in preferred embodiments there are two data streams being evaluated, e.g., one from the SAW sensor and another from the IMCell sensor.

Embodiments of the present invention do not initially monitor the raw data from sensors to classify the type of agent detected. Instead, the alarm status of the individual sensors is monitored by an agent classification routine 410. Once an alarm occurs, the system collects other concurrent alarms and resolves the class of agent present based on a combination of the alarms. The approach can be illustrated for two sensor types using the matrix of FIG. 5. The matrix (or one similar to it tailored to specific sensors) can be developed by evaluating the false alarm rate for the individual sensors and discounting the modes in which a particular sensor exhibits a higher false alarm rate while giving more weight to modes where a sensor exhibits a lower false alarm rate. In some embodiments, numerical weights are used.

Use of the data fusion process can improve the detection range of the instrument. During live agent tests the system was challenged with a number of agents at different concentrations and humidity ranges as shown in Table 1 below.

TABLE 1

| Agent | Concentration (mg/m3) | Humidity |
|---|---|---|
| GD | 0.09, 0.3, 1.3 | 10, 50, 90 |
| GA | 0.08. 0.04, 1.4 | 10, 50, 90 |
| HD | 0.7, 1.0, 9.7 | 10, 50, 90 |
| AC | 22 | 10, 50, 90 |

During these tests, the average overall alarm detection range for the individual sensors covered only 74.1% of the above conditions. However, using the data fusion process the fused system detection range extended over 96.4% of the above conditions. Data fusion provides significantly improved results over a greater range of operation.

Figure 6:
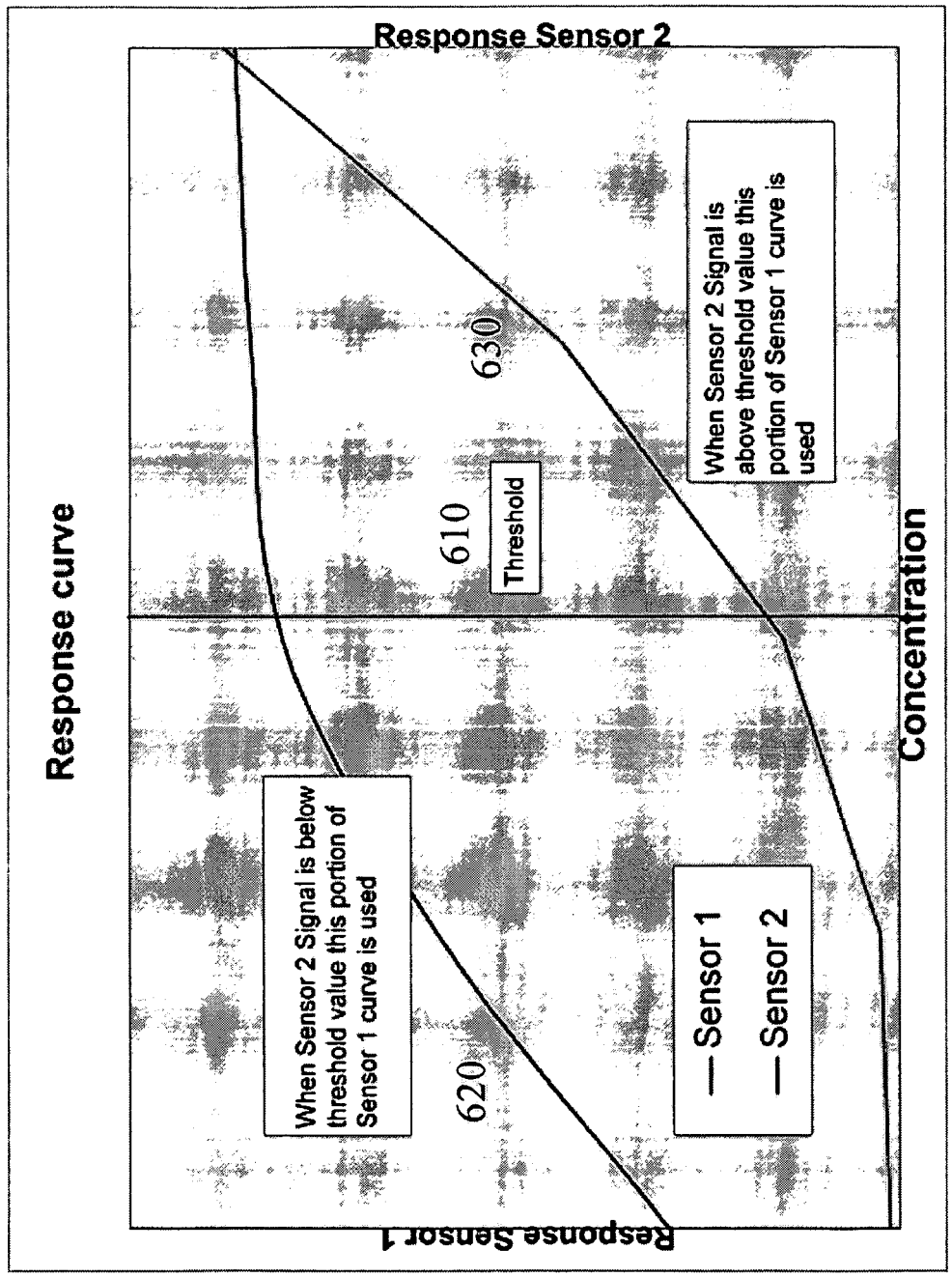
FIG. 6 illustrates the overlapping response curves for two notional sensors in a preferred embodiment of the invention.

Once the alarms are assessed in the first tier of data fusion, a second tier algorithm using raw data from the sensors is employed to determine the specific agent present 420 and the amount of the agent 430. The classification determined in the first tier allows specific evaluation and quantification methods to be applied more efficiently than if the classification were unknown. Some embodiments employ weighting factors among sensors based on the confidence of agent class and specific agent data. Preferred embodiments use known chemometric techniques for evaluating raw data from sensors. Typical sensors employed in preferred embodiments of the invention have a finite dynamic range over which the sensor operates in a fashion useful to measuring concentrations 430. FIG. 6 illustrates the overlapping response curves for two notional sensors in a preferred embodiment of the invention. In FIG. 6, for values of concentration under a threshold amount 610, Sensor 1 620 is used to quantify. For values over the threshold 610, Sensor 2 630 is used. Variations on this approach, including weighting the results of Sensor 1 620 and Sensor 2 630 responses are contemplated as being within the scope of the invention. The curves of FIG. 6 are for illustrative purposes only. It should be apparent that the vertical scale applicable to each curve need not be the same.

Some embodiments of the invention use sensors employing dynamic baseline correction. In preferred embodiments, one or more sensors with static baseline correction can be used to improve others with dynamic baseline correction. In certain forms of dynamic baseline correction, a sensor adjusts its baseline as a function of the ambient steady state value of chemical agent present. While this is advantageous in some circumstances, where the dynamic sensor is exposed to a slow continuous stream of agent below the detection limit this baselining mechanism could eliminate the accumulation of agents, e.g., desensitize the sensor and thereby the desensitize the system. This would cause false negative alarm rates to increase. By providing a feedback mechanism using the static baseline sensor alarms, the dynamic sensors' false negative alarm rate can be improved. When the static sensor alarms, the feedback mechanism triggers the dynamic sensor to reevaluate its alarm status by using clean environment baseline.

In preferred embodiments, a manifold supplies multiple sensors with air from one inlet source. The manifold balances the flow and volumetric demands of multiple sensors so that the higher demand is prevented from effectively diminishing the lower demand. In one fashion, this is accomplished by the design of obstructions, cavities, and the placement of some sensor's connections away from the source.

It should be recognized that various preferred embodiments and characteristics thereof that have been described are merely illustrative of the principles of this invention. Numerous modifications and adaptations thereof will be readily apparent to those skilled in the art without departing from the spirit and scope of the present invention.

The invention claimed is:

1. A chemical agent detector comprising:
   a lesser demand sensor,
   a greater demand sensor,
   an inlet; and
   a manifold, the manifold:
      between the inlet and the sensors, and
      comprising:
         a first intake associated with the lesser demand sensor,
         a second intake associated with a greater demand sensor; and
         at least one restrictor;
      wherein:
         the first intake is placed closer to the inlet than the second intake, and
         the second intake is isolated from the inlet by the at least one restrictor within the manifold.

2. The chemical agent detector of claim 1, wherein the intakes and restrictor are sized and positioned such that the ratio between:
   the conductance of the path from the inlet to the greater demand sensor, and
   the conductance of the path between the sensors, is greater than one.

3. The chemical agent detector of claim 2, wherein the ratio is substantially greater than one.

4. The chemical agent detector of claim 2, wherein the ratio is greater than ten.

5. The chemical agent detector of claim 2, wherein the ratio is greater than 50.

6. A chemical agent detector comprising:
   a lesser demand sensor;
   a greater demand sensor;
   an inlet;
   an outlet; and
   a manifold, the manifold comprising:
      a first intake associated with the lessor demand sensor;
      a second intake associated with a greater demand sensor; and
      at least one restrictor to isolate the second intake associated with the greater demand sensor from the inlet.

7. The chemical agent detector of claim 6 wherein the inlet and the outlet may be the same.

8. The chemical agent detector of claim 6 wherein
   the first intake is placed closer to the inlet than the second intake.

9. The chemical agent detector of claim 8 wherein the sensors overlap in areas of effectiveness.

10. The chemical agent detector of claim 8 wherein the sensors are mounted in a chassis.

11. The chemical agent detector of claim 10 wherein the chassis is sized to be hand-held.

12. The chemical agent detector of claim 10 further comprising a polycarbonate-protected display.

13. The chemical agent detector of claim 10 further comprising a speaker.

14. The chemical agent detector of claim 10 further comprising a processor card.

15. The chemical agent detector of claim 10 further comprising a battery compartment containing a battery.

* * * * *